United States Patent [19]
Hoenes et al.

[11] Patent Number: 5,382,523
[45] Date of Patent: Jan. 17, 1995

[54] USE OF SPARINGLY SOLUBLE SALT OF A HETEROPOLY ACID FOR THE DETERMINATION OF AN ANALYTE, A CORRESPONDING METHOD OF DETERMINATION AS WELL AS A SUITABLE AGENT THEREOF

[75] Inventors: Joachim Hoenes, Zwigenberg; Hans Wielinger, Weinheim; Volker Unkrig, Ladenburg, all of Germany

[73] Assignee: Boehringer Mannheim GmbH, Mannheim, Germany

[21] Appl. No.: 45,203

[22] Filed: Apr. 13, 1993

Related U.S. Application Data

[62] Division of Ser. No. 620,697, Dec. 3, 1990, Pat. No. 5,240,860.

[30] Foreign Application Priority Data

Dec. 2, 1989 [DE] Germany .................. 3940010

[51] Int. Cl.⁶ .................. C12Q 1/54; C12Q 1/00; C12Q 1/34; C12Q 1/26
[52] U.S. Cl. .................. 435/14; 435/4; 435/18; 435/25; 436/111; 436/112; 436/113
[58] Field of Search .................. 435/14, 4, 18, 25; 252/435; 436/113, 111, 112

[56] References Cited
U.S. PATENT DOCUMENTS

| | | | |
|---|---|---|---|
| 3,016,292 | 1/1962 | Bauer et al. | 435/14 |
| 4,364,844 | 12/1982 | Umemura et al. | 252/435 |
| 4,681,841 | 7/1987 | Matsumoto et al. | 435/14 |
| 4,952,495 | 8/1990 | Belly et al. | 435/14 |
| 5,240,860 | 8/1993 | Hoenes et al. | 436/111 |

*Primary Examiner*—Michael G. Wityshyn
*Assistant Examiner*—Louise N. Leary
*Attorney, Agent, or Firm*—Nikaido Marmelstein Murray & Oram

[57] ABSTRACT

A sparingly soluble salt of a heteropoly acid is used for the determination of an analyte which is an aromatic amine rich in electrons or together with another substance leads to such an amine. The analyte is determined by means of the heteropoly blue color formed.

8 Claims, 4 Drawing Sheets

Fig.1
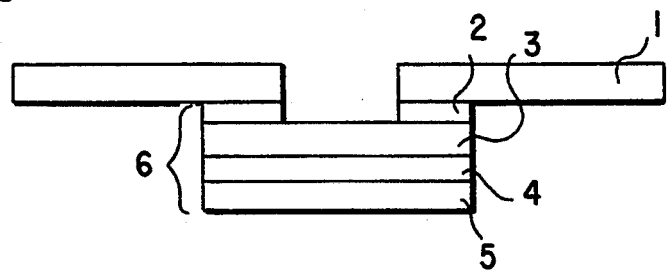
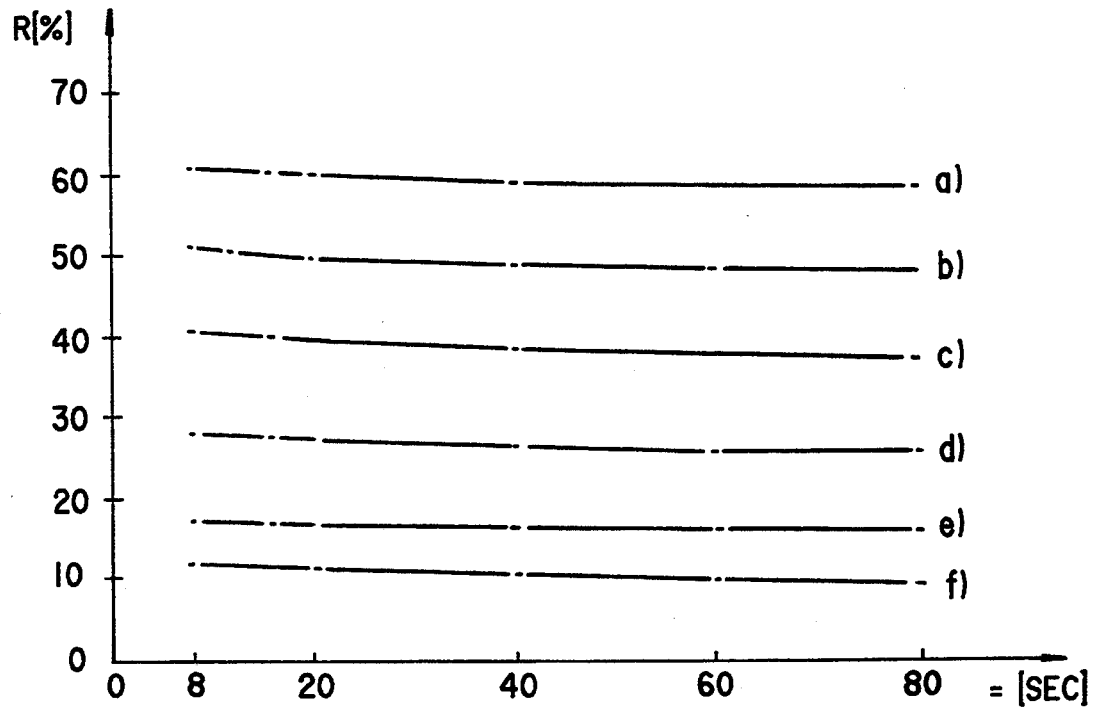
Fig.2

USE OF SPARINGLY SOLUBLE SALT OF A HETEROPOLY ACID FOR THE DETERMINATION OF AN ANALYTE, A CORRESPONDING METHOD OF DETERMINATION AS WELL AS A SUITABLE AGENT THEREOF

This is a division of application Ser. No. 07/620,697 filed Dec. 3, 1990 now U.S. Pat. No. 5,240,860.

The invention concerns the use of a sparingly soluble salt of a heteropoly acid for the determination of an analyte. In addition the invention concerns a method for the determination of an analyte by means of heteropoly blue formation as well as a suitable agent therefor. Finally, the invention also concerns the use of a sparingly soluble salt of a heteropoly acid for the production of an agent for the determination of an analyte by means of heteropoly blue formation.

Heteropoly acids are inorganic polyacids which have at least two different central atoms. They are formed from polybasic oxo acids of a metal such as molybdenum, tungsten, vanadium and a non-metal or metal such as phosphorus, silicon, arsenic, iodine, iron, manganese, cobalt as partially mixed anhydrides. Examples are phosphomolybdic acid and phosphotungstic acid. Heteropoly acids are soluble in water. They are, however, only stable in acid solution.

Heteropoly acids of molybdenum and tungsten are reagents which have been known for a long term. They are used analytically to determine phosphate and also to detect arsenic or silicate by formation of the correponding heteropoly acids with molybdate or tungstate and subsequent reduction of the heteropoly acid to a blue dye, the so-called heteropoly blue. The colour is based on the absorbance of light by the transition of electrons between pentavalent and hexavalent molybdenum or tungsten. The heteropoly blue from heteropoly acids is in each case a dye with a high absorbance which has a very broad absorption maximum depending on the wavelength. This is typical for charge-transfer absorption bands.

Heteropoly acids are known which can be used for the detection of reducing compounds by formation of heteropoly blue. In "Spot Tests in Organic Analysis" by F. Feigl, Elsevier Publishing Company, 5th Edition, 1956, pages 128 and 129, it is described that 12-molybdophosphoric acid is reduced to molydenum blue by many reducing substances. Since this test reaction is unspecific it is recommended that the sample to be examined is made alkaline followed by an ether extraction in order to achieve a certain selectivity. The ether extract then mainly contains aromatic nitrogenous bases and ether-soluble neutral substances. Acidic substances remain dissolved in the aqueous phase.

It is known from P. B. Issopoulos, Pharm. Acta Helv. 64, 82 (1989) that certain drugs which contain an o-hydroquinone structure, such as e.g. methyl-dopa, act reductively on molybdophosphoric acid in sulphuric acid solution and lead to the formation of molybdenum blue.

The use of phosphotungstic acid for the detection of uric acid is described in M. L. Matheke et el., Clin. Chem. 33, 2109–2110 (1987). The reductive formation of tungsten blue serves as an indicator for the presence of uric acid. The presence of drugs which act reductively interferes with the test reaction.

In B. Klein et al., Clin. Chem. 12, 816–823 (1966) a determination of glucose in serum or plasma is disclosed which is based on the following reaction sequence:

Glucose is oxidised by potassium hexacyanoferrate (III) whereby the potassium hexacyanoferrate (II) formed acts reductively on phosphomolybdic acid and leads to the formation of molybdenum blue. Since serum and plasma can contain different amounts of uric acid, drugs or other substances which act reductively such as, for example, bilirubin or glutathione they are certain to interfere with this method.

The main disadvantage of all previously known analytical methods which rely on the reductive formation of heteropoly blue from heteropoly acids is above all the non-specificity of the respective test reaction. Very many reducing substances can interfere since they also lead to the formation of heteropoly blue. In addition, heteropoly acids are only stable under acidic conditions. This greatly limits their range of applications. In particular, the coupling of heteropoly blue formation to enzymatic reaction steps in order to specifically detect and specifically determine substances is hitherto unknown. Enzymatic methods of determination are, however, often necessary, especially for the detection of constituentis of body fluids such as blood, serum, plasma, urine, etc.

The object of the present invention was to make use of the formation of heteropoly blue as a test reaction and for substances in particular for substances in body fluids and in particular in combination with enzymatic reaction steps. Accompanying substances which act reductively should not interfere in this process and the test reaction and determination reaction determination reaction for substances, in particular for substances in body fluids and in particular in combination with enzymatic reaction steps. Accompanying substances which act reductively should not interfere in reaction and determination reaction this process and the test reaction and determination reaction should proceed at a pH value necessary for enzymatic reactions. In addition, it should be possible to rapidly carry out the test reaction and determination reaction.

This object is achieved by measures as characterized in the claims.

It was found that a sparingly soluble salt of a heteropoly acid can be used advantageously for the determination of an analyte especially if the analyte is an aromatic amine rich in electrons or if, together with a further substance, it leads to such.

The method according to the present invention for the determination of an analyte by means of heteropoly blue formation is characterized in that the analyte is reacted with a substance which leads to the formation of an aromatic amine rich in electrons which is brought into contact with a sparingly soluble salt of a heteropoly acid. Of course, the method according to the present invention can itself also be used to determine an aromatic amine rich in electrons by bringing a solution of this amine into contact with a sparingly soluble salt of a heteropoly acid.

The underlying object of the invention is also achieved for the production of an agent for the determination of an analyte by heteropoly blue formation.

According to the present invention an agent is provided for the determination of an analyte by heteropoly blue formation which is characterized in that it contains a substance which together with the analyte leads to an aromatic amine rich in electrons and in addition a sparingly soluble salt of a heteropoly acid or substances which yield such a salt on contact. If the agent according to the present invention is to serve directly to determine an aromatic amine rich in electrons, it suffices if it contains a sparingly soluble salt of a heteropoly acid or substances which yield such a salt on contact in a liquid medium or in carrier bound form.

According to the present invention a sparingly soluble salt of a heteropoly acid can be used for the determination of an analyte. In the sense of the present invention a sparingly soluble salt of a heteropoly acid is understood primarily as such a salt of a heteropoly acid which is not at all or only very slightly soluble in water, or aqueous media such as buffer or body fluids such as, for example, blood, plasma, serum, urine or saliva and also remains as such under the conditions for the test and colour formation. In particular the salt of a heteropoly acid is so sparingly soluble that the maximum amount which can be dissolved in a liquid sample would not alone be sufficient for the determination of the analyte contained therein.

Surprisingly, it turned out that such a sparingly soluble salt of a heterpoly acid is not only stable in the acidic pH range but also in the neutral and basic range, in particular up to about pH 10. It can thus be used in pH ranges in which most enzymes are active and therefore it can be used for the formation of heteropoly blue in combination with enzymatic reactions. A sparingly soluble salt of a heteropoly acid is also stable at higher temperatures, especially in the undissolved state. It has been shown that, despite the sparing solubility, an analyte can be detected and determined very rapidly by heteropoly blue formation with a salt of a heteropoly acid according to the present invention i.e. from within a few seconds up to a few minutes. A selective determination without interference by other substances which act reductively is possible by this means. This allows a sensitive method of measurement which does not require special specifications for the measuring instrument and can be easily followed visually which is in particular also due to the broad absorption maximum of the heteropoly blue which forms that ranges from about 550 to more than 1100 nm.

Salts of heteropoly acids which can be used according to the present invention are salts of heteropoly acids of molybdenum, molybdenum and tungsten, vanadium and molybdenum or vanadium and molybdenum and tungsten with phosphorus, arsenic, silicon or germanium as heteroatoms. Heteropoly acids of molybdenum with phosphorus or arsenic are particularly preferred. Phosphorus is especially preferred as the non-metallic atom. Molybdenum is especially preferred as the metallic atom. Emminently suitable are sparingly soluble salts of 12-molybdophosphoric acid, 18-molybdodiphosphoric acid, 12-molybdoarsenic acid, 18-molybdoarsenic acid, 11-molybdo-1-vanadophosphoric acid, 10-molybdo-2-vanadophosphoric acid and 9-molybdo-3-vanadophosphoric acid, in which 18-molybdodiphosphoric acid is particularly preferred because of its high colour yield on reduction to molybdenum blue.

Sparingly soluble salts of heteropoly acids are those which have cations larger than the ammonium ion, $NH_4^+$. Preferred cations can be represented by the general formula I $$R^1R^2R^3R^4X^+ \qquad (I)$$

in which $R^1$, $R^2$, $R^3$, $R^4$ are the same or different and denote an alkyl, aryl or aralkyl residue or hydrogen, if not all the residues are the same or in which two residues together form an alkylene residue and X represents a phosphorus or nitrogen atom.

In alkyl and aralkyl residues alkyl denotes a straight-chain or branched-chain residue containing 1–22 carbon atoms, preferably 1–6 carbon atoms. Aryl in aryl or aralkyl residues denotes an aromatic residue of 6 to 10 carbon atoms. Phenyl or naphthyl are particularly preferred.

The benzyl group is particularly preferred as the aralkyl residue.

An alkylene residue is a saturated or unsaturated carbon atom chain composed of 4–6, preferably 4 or 5 carbon atoms which are bound to X at both ends. Cations having the general formula I can contain two such alkylene residues. However, preferably only one alkylene residue is present.

X preferably denotes a nitrogen atom in the general formula I. Preferred cations in sparingly soluble salts of heteropoly acids can also be those from the group of aromatic heterocyclic compounds containing a quaternary nitrogen atom. Examples are pyridine or quinoline which carry an alkyl, aryl or aralkyl residue on their nitrogen atom whereby the definition of these residues as given above for the residues $R^1$, $R^2$, $R^3$, $R^4$ in the general formula I also applies.

A sparingly soluble salt of a heteropoly acid according to the present invention can be obtained for example by reacting a heteropoly acid with a corresponding basic substance. For this purpose, at least one substance is usually employed as a solution, preferably an aqueous solution. However, both salt components can be added in a solid form to a liquid, in particular an aqueous liquid or vica versa.

An analyte denotes a substance to be determined. The invention has turned out to be especially suitable for substances which are present dissolved in a liquid, in particular an aqueous liquid. A sparingly soluble salt of a heteropoly acid can be used. Particularly advantageously for the determination of substances in body fluids such as, for example, blood, plasma, serum, urine or saliva. Possible analytes in this sense are for example glucose, cholesterol, lactate, NADH or ethanol. In principle, all those substances can be determined according to the present invention which together with one or more other compounds can be converted to such substances or which are themselves substances which, with regard to their redox potential and with regard to their kinetics, are able to reduce a sparingly soluble salt of a heteropoly acid to heteropoly blue within a few seconds up to a few minutes, preferably in less than three minutes. Surprisingly, it turned out that aromatic amines rich in electrons are capable of doing this. Above all, it is surprising that in doing so a selective determination is possible without interference by other compounds which act reductively.

An aromatic amine rich in electrons is understood as a compound which is richer in electrons than aniline and thus constitutes a stronger reducing agent than aniline. Aromatic amines which are rich in electrons have a redox potential of less than 0.6 V, preferably less than 0.45 V versus a normal hydrogen electrode. The magnitude of the redox potential alone is, however, not decisive. In addition, it is important that the respective substance is capable of rapidly reducing a sparingly soluble salt of a heteropoly acid to heteropoly blue i.e.

in less than about three minutes. For example, all aniline derivatives come into consideration which carry one or more +I or/and +M substituents such as hydroxy, alkyl, alkoxy, aryloxy, alkylthio, arylthio, amino, monoalkylamino and dialkylamino residues.

Alkyl, alkoxy, alkalthio, monoalkylamino and dialkylamino residues are residues in which alkyl represents a hydrocarbon residue with 1-6 carbon atoms, which can itself be substituted by a hydroxy group, an amino group substituted, if desired, once or several times by an alkyl with 1-6 carbon atoms, $PO_3H_2$, $SO_3H$ or $CO_2H$. The acid residues $PO_3H_2$, $SO_3H$ and $CO_2H$ can be present as such or in the form of a salt such as ammonium, alkaline or earth alkaline salts.

Aryloxy and arylthio residues are residues with 6-10 carbon atoms whereby phenoxy and phenylthio residues are particularly preferred.

Compounds are also understood as aniline derivatives which carry an unsubstituted amino group or an amino group substituted once or several times by an alkyl on an aromatic ring system which is anellated with one or several aromatic or/and alicyclic rings. In this connection, carbon-aromatic systems as well as heteroaromatics come into consideration as aromatic rings. Examples are anellated benzol or naphthaline rings or an anellated pyridine ring.

Alicyclic rings are understood as saturated or unsaturated cycloaliphatics with 5-7 carbon atoms, preferably 5 or 6 carbon atoms.

Possible alkyl substituents of the amino group can be hydrocarbon residues with 1-6 carbon atoms which in turn can be substituted by a hydroxy group, an amino group substituted, if desired, once or several times by an alkyl with 1-6 carbon atoms, $PO_3H_2$, $SO_3H$ and $CO_2H$. The acid residues $PO_3H_2$, $SO_3H$ and $CO_2H$ can be present as such or in the form of a salt such as ammonium, alkaline or alkaline earth salts.

Particularly suitable as aromatic amines rich in electrons are compounds having the general formula II

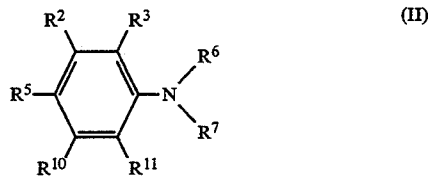

in which
- $R^5$ denotes hydroxy or amino, in which the amino group is substituted, if desired, once or twice by an alkyl residue, and the alkyl residue is itself substituted, if desired, by a hydroxy group, an amino group substituted, if desired, once or several times by alkyl, $PO_3H_2$, $SO_3H$ or $CO_2H$,
- $R^6$ and $R^7$ which are both the same or different and represent hydrogen or alkyl, in which the alkyl residue is substituted, if desired, by a hydroxy group, an amino group substituted, if desired, once or several times by alkyl, $PO_3H_2$, $SO_3H$ or $CO_2H$, and
- $R^8$, $R^9$, $R^{10}$ and $R^{11}$ are the same or different and denote hydrogen, alkyl, alkoxy, alkylthio, aryloxy, arylthio, halogen, carboxy, carboxyalkyl or alkoxycarbonyl.

Alkyl residues and "alkyl" in alkylthio, carboxyalkyl and alkoxycarbonyl residues are hydrocarbon residues with 1-6 carbon atoms. Residues with 1-3 carbon atoms are particularly preferred. Alkoxy residues are also hydrocarbon residues with 1-6 carbon atoms. Residues with 1-3 carbon atoms are particularly preferred. Aryloxy and arylthio residues are residues with 6-10 carbon atoms, whereby phenoxy and phenythio residues are particularly preferred. Halogen denotes fluorine, chlorine, bromine or iodine. Chlorine and bromine are preferred halogen substituents.

Acid residues $PO_3H_2$, $SO_3H$ or $CO_2H$ can be present as such or in the form of a salt such as ammonium, alkaline or alkaline earth salts.

Ammonium salts are those which contain the ammonium ion, $NH_4^+$, or those that contain an ammonium cation substituted once or several times by alkyl, aryl or aralkyl residues. Alkyl in alkyl and aralkyl residues denote a hydrocarbon residue with 1-6 carbon atoms. Aryl in aryl and aralkyl residues is an aromatic ring system consisting of 6-10 carbon atoms, whereby phenyl is preferred. A preferred aralkyl residue is benzyl.

Alkaline salts are preferably those of lithium, sodium or potassium. Alkaline earth salts are preferably those of magnesium or calcium.

Aromatic amines rich in electrons can be determined directly with a sparingly soluble salt of a heteropoly acid by formation of heteropoly blue. Substances can also be determined which by means of a chemical or enzymatic reaction convert a further substance into an aromatic amine rich in electrons in a stoichiometric manner. Those substances can be used for example as a reaction partner which already contain a skeleton of an aromatic amine rich in electrons and which can be released from them by a chemical or enzymatic reaction with the analyte to be determined. Such compounds are to be preferably understood as those which by hydrolysis lead to an aromatic amine rich in electrons. Amides, esters or glycosides or aromatic amines rich in electrons may be mentioned as examples. Analytes which can be determined in this way are preferably enzymes which catalyse the conversion of suitable substrates into aromatic amines rich in electrons, in particular hydrolases such as enzymes which cleave amide bonds and/or peptide bonds, enzymes which cleave ester bonds- whether bonds of carboxylic acid, phosphoric acid or sulphuric acid—and enzymes which cleave glycosidic bonds, and in addition transferases which catalyse the transfer of groups such, as for example γ-glutamyl-transferase.

In addition, substances can for example be determined which can be enzymatically oxidised, whereby such compounds are used as electron acceptors which on reduction yield aromatic amines rich in electrons. A multitude of oxidoreductases are known, especially for substances in body fluids such as blood, plasma, serum, urine or saliva, which each specifically recognises certain substances and which oxidises these substances in the presence of a functioning electron acceptor.

Flavin-dependent oxidases such as L- and D-amino acid oxidase, cholesterol oxidase, glucose oxidase, glycerol-3-phosphate oxidase, lactate oxidase or pyruvate oxidase and non-NAD(P)-dependent dehydrogenases such as the pyrroloquinoline-quinone-dependent glucose dehydrogenase or also diaphorase (NADH: dye-oxidoreductase) may be mentioned as examples.

In the case of oxidoreductases, in particular oxidases and non-NAD(P)-dependent dehydrogenases, electron acceptors for enzymatic oxidations can be used which are reduced to an aromatic amine rich in electrons by the enzymatic oxidation of the enzyme substrate. In this way those substances, which are oxidised enzymatically, can be detected and determined by heteropoly blue formation by bringing the aromatic amine rich in electrons which forms into contact with a sparingly soluble salt of a heteropoly acid.

In this connection, electron acceptors which are advantageous within the scope of the present invention are, in particular, aromatic nitroso compounds, oximes and hydroxylamines. Aromatic nitroso compounds and oximes are particularly preferred. Those nitroso compounds and oximes as described in copending application Ser. No. 07/390,946, filed Aug. 9, 1989, now U.S. Pat. No. 5,206,147, the disclosure of which is incorporated herein by reference, are particularly preferred.

In order to carry out the determination of an analyte by formation of heteropoly blue acccording to the present invention it suffices to react the analyte with a substance as described above, to convert it to an aromatic amine rich in electrons and to bring it into contact with a sparingly soluble salt of a heteropoly acid. If the aromatic amine rich in electrons is itself the analyte to be determined directly, this is brought into contact with a sparingly soluble salt of a heteropoly acid without previous chemical or enzymatic reactions.

As a rule, at least the aromatic amine rich in electrons which acts on the salt of the heteropoly acid is present in a soluble form, preferably in aqueous solution, for example, water, buffer or body fluid. If the analyte to be determined is not itself an aromatic amine rich in electrons, then the compound which together with the analyte is necessary to produce an aromatic amine rich in electrons is preferably also soluble in an aqueous liquid. It can be added to the sample before contact with a sparingly soluble salt of a heteropoly acid. It can also, however, first be brought into contact with the sample to be examined together with the sparingly soluble salt of a heteropoly acid or it can even be brought into contact in a final step. The order chosen depends on the individual case and can be decided by the expert on the basis of his general technical knowledge or by a few optimization experiments. The substance necessary to produce an aromatic amine rich in electrons can be added to an aqueous sample in a solid or dissolved form.

The substance which together with the analyte to be determined yields an aromatic amine rich in electrons must be brought into contact with the sample in an amount which is large enough that the entire analyte can be made to react. A 2–10-fold excess is preferably used.

The sparingly soluble salt of a heteropoly acid can be brought into contact as a solid substance with the sample to be examined. It can, however also be present as a suspension in a fluid, preferably an aqueous fluid, whereby the suspension is then mixed with the sample to be examined in order to carry out the determination. When the analyte to be determined is present heteropoly blue forms which is sparingly soluble in water and can be detected by means of its intensive colour. In order to carry out a quantitative determination it is possible to separate the heteropoly blue, which is sparingly soluble in water, and the non-reacted heterouily acid salt from the liquid, for example by centrifugation, subsequently to dissolve it in a suitable solvent, such as for example dimethylsulphoxide, and to measure the concentration of the heteropoly blue dye photometrically with the aid of standard solutions or calibration curves, if desired, and thus finally to determine the concentration of the analyte to be determined.

The sparingly soluble salt of a heteropoly acid must be present in such a large amount that the aromatic amine rich in electrons present in the sample, or which forms, leads to the formation of heteropoly blue which can be quantitatively related to the amount of analyte to be determined or the aromatic amine rich in electrons. In principle, the amount of a sparingly soluble salt of a heteropoly acid used must therefore be such that an increase in the amount of amine leads to an increase in the amount of heteropoly blue up to the highest relevant concentration of the aromatic amine rich in electrons.

An agent according to the present invention for the determination of an analyte by formation of heteropoly blue contains a substance which together with the analyte leads to an aromatic amine rich in electrons and also contains a sparingly soluble salt of a heteropoly acid. Such an agent can be used for example as a suspension or as a lyophilisate, powder mixture or can be pressed into a tablet. The constituents can be present next to each other or separated whereby each of the constituents can be processed into its most expedient form. It is indeed also possible that an agent according to the present invention does not contain a sparingly soluble salt of a heteropoly acid which is ready to use but instead contains separately the components needed to prepare such salt i.e. for example a heteropoly acid and a cationic or basic compound, both of which are first brought into contact immediately before the determination reaction according to the present invention and then yield the corresponding salt. It is particularly advantageous if the agent according to the present invention contains a sparingly soluble salt of a heteropoly acid in a finely dispersed form so that it has a large reactive surface. If desired, the agent according to the present invention can also contain further reagents such as buffers and auxiliary agents such as for example wetting agents, stabilizers, builders etc. If the analyte to be determined is itself an aromatic amine rich in electrons one of course does not need a substance for the agent according to the present invention which together with the analyte first leads to an aromatic amine rich in electrons.

The determination of an analyte according to the present invention can be carried out in a particularly advantageous manner with a so-called dry test. Devices which are suitable for carrying cut a dry test are known to the expert for example from U.S. Pat. Nos. 4,312,834; 4,820,489; 4,876,076 and 4,935,346. They can be denoted test carriers. In this case the reagents necessary for carrying out a test are present in a dry form, i.e. not dissolved in a liquid, for example in or on an absorptive material such as, for example, paper, an open film according to U.S. Pat. No. 4,312,834, a glass fibre fleece or a porous plastic membrane to mention only a few possible materials, or in or on a material capable of swelling such as e.g. a corresponding plastic film, gelatins or cellulose.

When the sample fluid is applied to the test carrier or the test carrier is dipped into the sample fluid a liquid environment forms in the test carrier within which the test reaction proceeds. The formation of colour caused by the reaction can be evaluated visually or photometrically e.g. by reflection photometry.

In order to produce the agent according to the present invention in a carrier-bound form, a suitable carrier material such as filter paper, cellulose or a plastic fibre fleece is impregnated with solutions or/and suspensions of the reagents necessary for the production of test carriers in highly volatile solvents such as e.g. water, methanol, ethanol or acetone. This can be carried out in an impregnation step. It is often expedient to carry out the impregnation in several steps in which solutions or/and suspensions are used which each contain part of the constituents of the final agent. Thus, for example, the sparingly soluble salt of a heteropoly acid can be applied to the carrier material from a suspension in a first step and in a second step the substance which together with the analyte leads to an aromatic amine rich in electrons is applied from a solution which, if desired, contains buffer and other additives. The carrier material treated in this way can be used as such or it can be glued to holders or onto stiff plastic foils in a known manner in order to improve the handling.

Instead of a multiple impregnation of the same carrier material, the reagents of the agent according to the present invention can also be distributed on different carrier materials which, when carrying out the determination of analyte, are brought into a contact which enables an exchange of fluids.

As an alternative to impregnation of the production of carrier-bound test agents, solutions can be prepared from film formers i.e. from polymers or from polymer dispersions which are so viscous that films can be produced from them according to known production processes such as knife-coating, roll-coating etc. The reagents and, if desired, buffer substances and auxiliary agents are integrated into these solutions. The coating masses are applied to carrier foils, dried and the final films are, for example, processed into test strips.

Examples of preferred test carriers are shown in FIG. 1 and 6. The other FIGS. 2-5 and 7 show diagrams of the dependence of the reflection in percent on time, wavelength, or analyte concentration which were obtained using the test carriers according to FIG. 1 or FIG. 6.

BRIEF DESCRIPTION OF THE DRAWINGS

FIG. 1: shows a cross-section through a preferred test carrier.

FIG. 2: is a diagram which shows the dependence of the reflection in percent on the time in seconds after sample application to a test carrier according to FIG. 1 for samples a)-f) each having a different glucose concentration.

Figure 3:
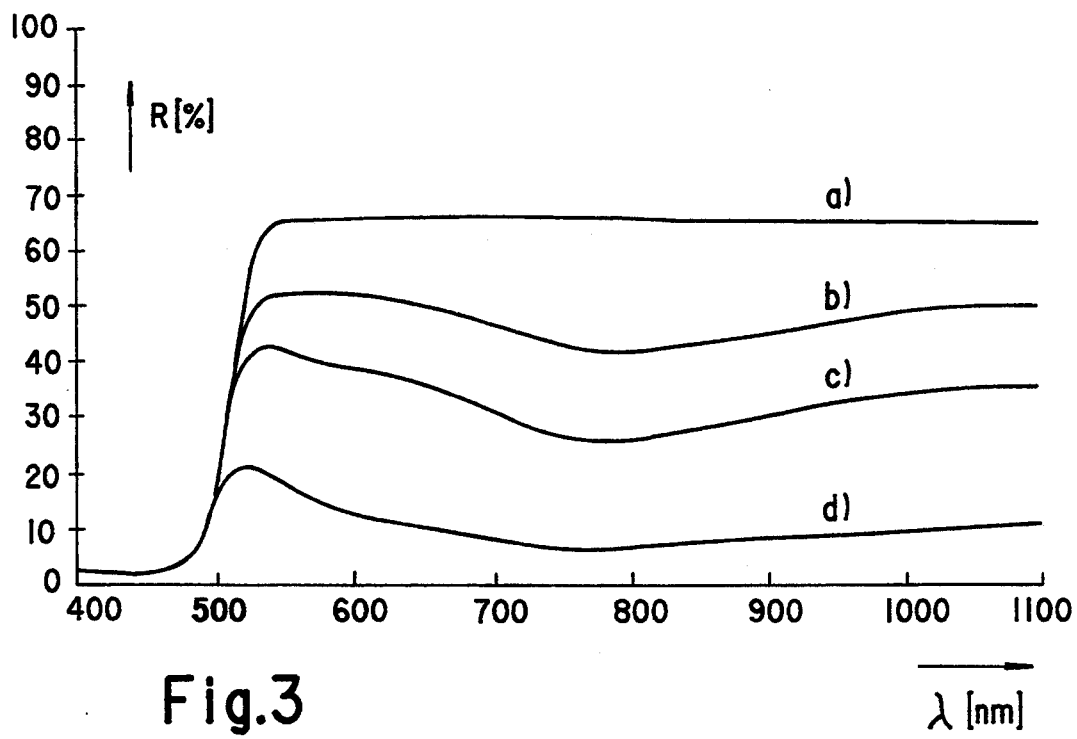
FIG. 3: is a diagram showing the dependence of the reflection in percent on the wavelength in nanometers for samples a)-f) having different glucose concentrations when using a test carrier according to FIG. 1.

The following Examples show some of the possible variants of the method for the determination of an analyte by heteropoly blue formation. They are not meant to represent a limitation of the invention to these embodiments. The Figures are elucidated further in the Examples.

EXAMPLE 1

Detection of glucose with 18-molybdodinhosphate

A test carrier is manufactured according to FIG. 1. It consists of a polyester foil 350 $\mu$m thick (Melinex, ICI, Frankfurt, German Federal Republic) as the carrier foil (1) and measures 2×3 cm. There is a hole of 6 mm diameter in the centre of the carrier foil. The reagent carrier (6) consisting of a 200 $\mu$m thick transparent polycarbonate foil (5) (Pokalon, Lonza, Rheinfelden, German Federal Republic), a first reagent layer (4) and a second reagent layer (3) is mounted over the hole in the carrier foil using transfer adhesive (2) in such a way that a sample liquid applied through this hole first comes into contact with the second reagent layer. The reagent carrier measures 2×1 cm.

The reagent carrier (6) is manufactured as follows:
First reagent layer:
113 g re-distilled water,
36.3 g 2% by weight Xanthan, a polysaccharide (Keltrol F, Kelco, Okla., USA) in 0.2M citrate buffer, pH 7.0
69 g Propiofan 70 D, a copolymers of vinyl acetate and vinyl propionate (BASF, Ludwigshafen, German Federal Republic)
15 ml 15% by weight sodium nonylsulphate in water
6 g polyvinylpyrrolidone (Kollidon 25, BASF, Ludwigshafen, German Federal Republic)
3.9 g tetrabutylammonium chloride
12 g 18-molybdodiphosphoric acid (prepared according to G. Brauer, "Handbuch der präparativen anorganischen Chemie", Publisher Enke, Stuttgart, 1954) in 15 g water
63 g Celatom MW 25, kieselguhr or diatomaceous earth (Eagle Picher, Cincinnati, Ohio, USA)
are stirred to a homogeneous mass and knife-coated in a thickness of 150 $\mu$m onto the tranparent foil (5). It is dried for one hour at 60° C.

Second reagent layer:
20 g re-distilled water,
16 g titanium dioxide RN 56 (Kronos-Titan GmbH, Leverkusen, German Federal Republic)
36.3 g 2% by weight Keltrol F (Kelco, Oklahoma, USA) in 0.2M citrate buffer, pH 6.0
69 g Propiofan 70 D (BASF, Ludwigshafen, German Federal Republic)
15 ml 15% by weight sodium nonylsulphate in water
6 g Kollidon 25 (BASF, Ludwigshafen, German Federal Republic)
188 g water
63 g CelatomMW 25 (Eagle-Picher, Cincinnati, Ohio, USA)
400 mg N,N-bis-(2-hydroxyethyl)-p-nitrosoaniline×HCl in 20 g water
2 g glucose oxidase (200 U/ml) in 12 q water
are stirred to a homogeneous mass and knife-coated in a thickness of 400 $\mu$m onto the first reagent layer. Air bubbles are removed by gentle blowing and the coating is dried for one hour at 60° C.

At time t=0 human plasma with a) 0 mg glucose/dl, b) 47.5 mg glucose/dl, c) 108.7 mg glucose/dl, d) 200.8 mg glucose/dl, e) 392.3 mg glucose/dl and f) 766 mg glucose/dl are each applied to a separate test carrier which is manufactured as described above. The remission in % is measured at 950 nm. The first measurement is after eight seconds and further measurements are at four second intervals. A diagram according to FIG. 2 is obtained by plotting the remission (R) in precent against time (t). The colour formation and decrease in remission is already almost complete at the time of the first measurement. A stable end-point results which can be measured at almost any time after the start.

FIG. 3 is obtained when samples with a glucose concentration of a) 0 mg/dl, b) 100 mg/dl, c) 240 mg/dl and d) 800 mg/dl, are measured with a test carrier according to FIG. 1, manufactured as described above, at different wavelengths and the remission (R) in percent is plotted against the wavelength ($\lambda$) in nm in a diagram. The spectra in this diagram clearly show that any wavelength between 550 nm and more than 1100 nm can be used to measure the glucose concentration. As a result of the relatively flat spectrum, the tolerance for variations in the wavelength is very high.

EXAMPLE 2

Specificity of the glucose detection with 18-molybdodiphosphate

The interfering substances listed in Table 1 are added in the concentrations given to human plasma with a) 0 mg glucose/dl ($C_{Gluc}=0$) and b) 110 mg glucose/dl ($C_{Gluc}$110 mg/dl). If such human plasma are examined with a test carrier according to FIG. 1 which is manufactured and described as in Example 1, then the remission values in percent (% R) at 660 nm are found as cited in Table 1.

TABLE 1

| Interfering substance | Final concentration | $C_{Gluc} = 0$ % R | $C_{Gluc} = 110$ mg/dl % R |
|---|---|---|---|
| none (reference) | 0 | 60.3 | 43.0 |
| NaOH | 1 mM | 59.9 | 42.5 |
| uric acid | 10 mg/dl | 59.5 | 42.4 |
| | 20 mg/dl | 60.1 | 42.4 |
| lactate | 100 mg/dl | 59.7 | 43.2 |
| | 300 mg/dl | 60.2 | 42.8 |
| bilirubin | 10 mg/dl | 60.0 | 42.7 |
| | 20 mg/dl | 61.5 | 43.0 |
| glutathione | 1 mM | 59.3 | 43.0 |
| | 5 mM | 59.4 | 43.8 |
| methyldopa | 10 mg/dl | 59.5 | 43.1 |
| | 100 mg/dl | 59.0 | 42.1 |
| dobesylate | 20 mg/dl | 59.4 | 41.8 |
| gentisic acid | 50 mg/dl | 59.6 | 43.0 |
| aspirin | 5 mg/dl | 59.9 | 42.1 |
| | 60 mg/dl | 60.0 | 42.0 |

No significant interferences are found in human plasma (0 and 110 mg/dl) independent of the glucose concentration.

The results obtained using a test carrier according to FIG. 1, which is manufactured according to Example 1 and is identical to the test carrier described there except for the use of tetrabutylammonium chloride which is omitted for the reference carrier, show a great scatter and poor reproducibility because the 18-molybdophosphoric acid used decomposes at pH values above 5.5. In addition, reducing substances interfere here by additional colour formation.

EXAMPLE 3

Test carrier for the detection of glucose based on 12-molybdophosphate

Figure 4:
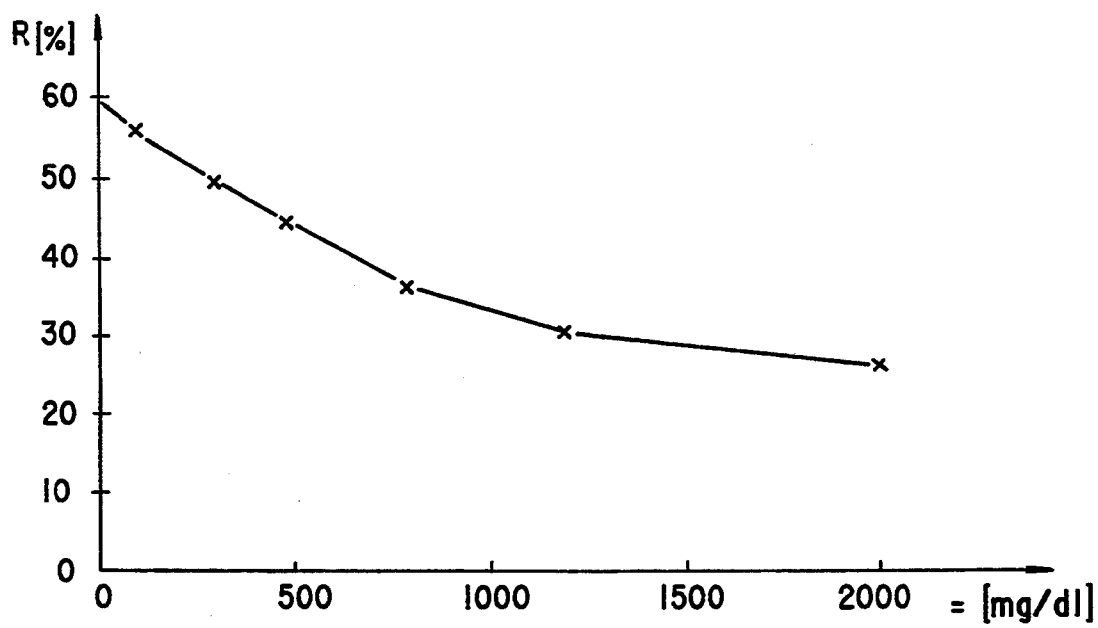
FIG. 4: is a diagram showing the dependence of the reflection in percent on the glucose concentration when measured with a test carrier according to FIG. 1.

If 18-molybdodiphosphoric acid in the recipe of Example 1 is replaced by the same amount of 12-molybdophosphoric acid (Fluka, Buchs, Switzerland) a test carrier is obtained which shows a weaker formation of colour in the presence of glucose and which is particularly well-suited for higher glucose concentrations. The curve according to FIG. 4 is obtained by use of samples of different but known glucose concentration (C) and measuring the respective remission (R) in percent at 650 nm. An identical curve is obtained if measured at 950 nm.

Similar results are obtained with 12-molybdoarsenate (V), 18-molybdodiarsenate (V), 11-molybdo-1-vanadophosphate, 10-molybdo-2-vanadophosphate and 9-molybdo-3-vanadophosphate which can all be prepared according to G. Brauer, "Handbuch der präparativen anorganischen Chemie", Publisher Enke, Stuttgart (1954). The names and formulae of the heteropoly acids as well as the absorbance maxima of the corresponding heteropoly blue are shown in the following Table 2.

TABLE 2

Heteropoly blue from different heteropoly acids

| starting substance | formula | absorption maximum of the heteropoly blue |
|---|---|---|
| 12-molybdophosphoric acid | $H_3(PMo_{12}O_{40}) \times$ n $H_2O$ | 725 nm |
| sodium-18-molybdodiphosphate | $Na_6(P_2Mo_{18}O_{62}) \times$ 42 $H_2O$ | 693 nm |
| potassium-12-molybdoarsenate (V) | $K_3(AsMo_{12}O_{40}) \times$ n $H_2O$ | 840[a] or 652 nm[b] |
| sodium-18-molybdodiarsenate (V) | $Na_6(As_2Mo_{18}O_{62}) \times$ 23 $H_2O$ | 672 nm |
| 11-molybdo-1-vanadophosphoric acid | $H_4(PMo_{11}VO_{40}) \times$ n $H_2O$ | 665 nm |
| 10-molybdo-2-vanadophosphoric acid | $H_5(PMo_{10}V_2O_{40}) \times$ n $H_2O$ | 620 nm |
| 9-molybdo-3-vanadophosphoric acid | $H_6(PMo_9V_3O_{10}) \times$ n $H_2O$ | 780 nm |

[a] litte reducing agent (glucose)
[b] much reducing agent (glucose)

EXAMPLE 4

Test carrier for the determination of NAD(P)H

Figure 5:
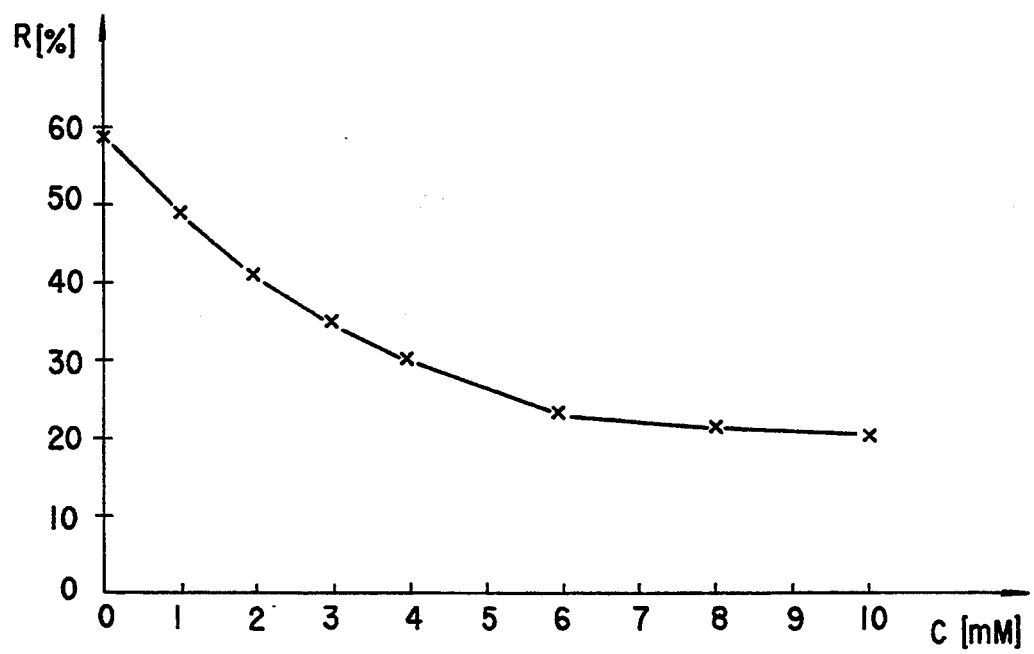
FIG. 5: is a diagram showing the dependence of the reflection in percent on the NADH concentration when measured with a test carrier according to FIG. 1.

If the glucose oxidase in the recipe of Example 1 is replaced by the same amount of diaphorase, a test carrier is obtained for the detection of NAD(P)H. The curve of FIG. 5 is obtained from samples with known concentration of NADH and measurement of the reaction in percent at 660 nm. This curve can serve as a calibration curve for the determination of unknown NADH concentrations.

Methods for the formation of NAD(P)H from an NAD(P)dependent dehydrogenase, a corresponding substrate and NAD(P) are known. Thus, after a suitable preliminary reaction, the NADH-test carrier can be used to detect dehydrogenase substrates or to detect the dehydrogenases themselves.

EXAMPLE 5

Figure 6:
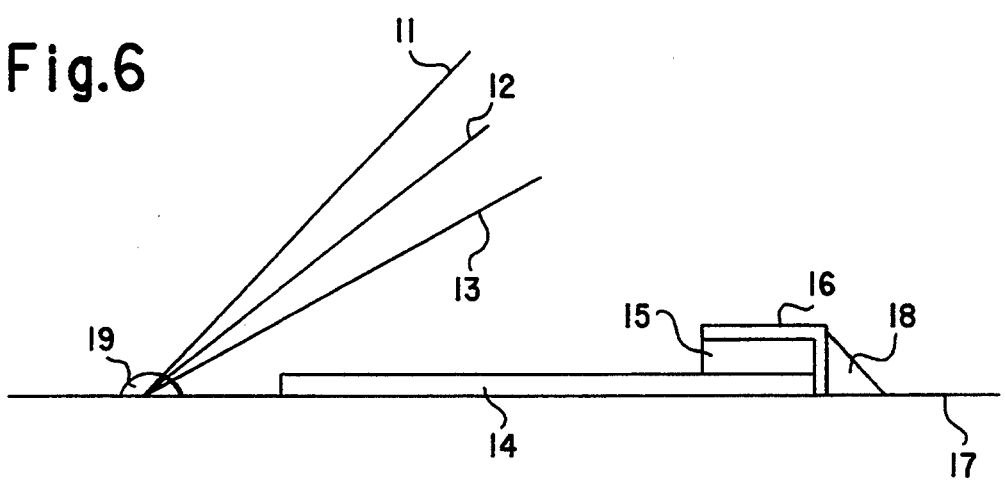
FIG. 6: is a cross-section through a further preferred test carrier.

Test carrier for the determination of ethanol by means of alcohol dehydrogenase and diaphorase as well as 18-molybdodiphosphate a) Manufacture of the test carrier A test carrier according to FIG. 6 is manufactured. This test carrier is constructed in such a way that the indicator system made of a homogenous suspension consisting of 4 ml 0.2M citrate buffer, pH 6.0
10 ml 10% by weight sodium nonylsulphate in water
60 mg tartrazine
0.1 g N,N-bis-(2-hydroxyethyl)-p-nitrosoaniline $\times$ HCl 6.8 ml 20% by weight 18-molybdodiphosphoric acid in water 1 g 25% by weight tetraethylammonium chloride in water 72 g 5% by weight Kollidon 25 (BASF, Ludwigshafen, German Federal Republic) in 50 mM citrate buffer, pH 6.0 is impregnated on an absorption pacer (Langfaser, Schoeller, Germsbach, German Federal Republic) and subsequently dried at 40° C. for 30 minutes.

The enzymes are incorporated on a separate paper (Langfaser, Schoeller, Germsbach, German Federal Republic). The paper is impregnated with a solution of 50 g 0.2M phosphate buffer, pH 7.0

48 g water 2 ml 10% by weight sodium nonylsulphate in water 6 g diaphorase (15 U/ml lyophilisate)

2 g alcohol dehydrogenase (250 U/ml lyophilisate), and subsequently dried at 40° C. for 20 minutes. The indicator paper (13) and enzyme paper (12) produced in this way is each cut into strips of 14×6 mm size.

A 16 mm long, 6 mm wide and 0.25 mm thick glass fibre fleece with an area weight of 25 g/m$^2$ serving as a transport fleece (14), a 6 mm wide, 6 mm long and 700 μm thick glass fibre fleece with an area weight of 60 g/m$^2$ serving as a fleece to separate off erythrocytes (15), as well as a protecting web (16) made of Scrynel PE28OHC red$^R$ (Züricher Beuteltuchfabrik AB, Ruschlikon, Switzerland) measuring 6×8 mm and having a mesh size of 280 μm are attached to a 350 μm thick, 9.8 cm long and 0.6 cm wide polyester foil (Melinex, ICI, Frankfurt, German Federal Republic) by means of a hot-setting adhesive strip (18) as indicated in FIG. 6. The enzyme paper (12) and indicator paper (13) are attached to the carrier foil (17) together with a 200 μm thick, 15 mm long and 6 mm wide transparent polycarbonate foil (Pokalon, Lonza, Rheinfelden, German Federal Republic) (11) by means of a drop of hot-setting adhesive (19) in such a way that (11), (12) and (13) do not touch each other but can under pressure be brought into contact with one another as well as into liquid contact with a liquid situated in the transport fleece (14).

b) Determination of ethanol

Figure 7:
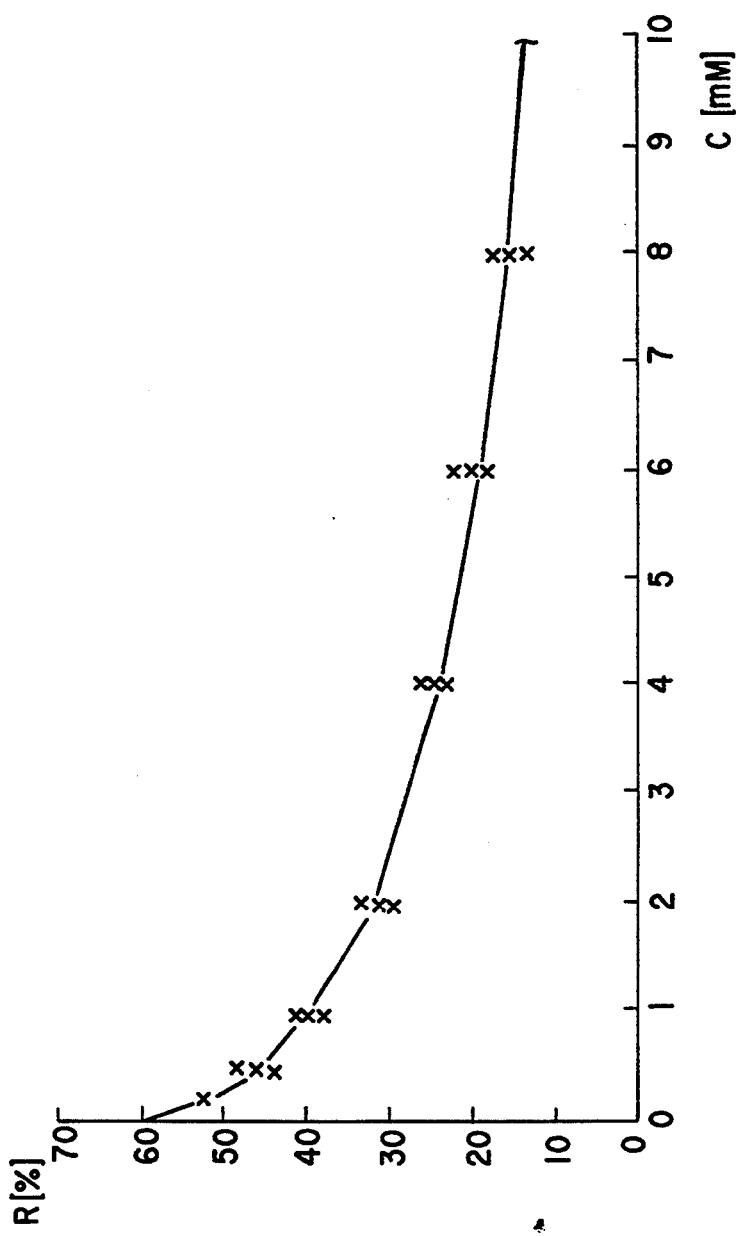
FIG. 7: is a diagram showing the dependence of the reflection in percent on the ethanol concentration when measured with a test carrier according to FIG. 6.

32 μl blood is applied to the protecting net (16) on the test carrier manufactured as under a) according to FIG. 6. After 60 seconds, the enzyme paper (12) and the indicator paper (13) are pressed onto the transport fleece (14) using pressure and onto the serum present therein. After 120 seconds the remission in percent at 642 nm is measured through the transparent foil (11). Using known, but different, ethanol concentrations in the blood a curve is obtained according to FIG. 7. This curve can serve as a calibration curve for the determination of an unknown ethanol concentration in a sample.

EXAMPLE 6

Determination of β-galactosidase (EC 3.2.1.23)

The following solutions are prepared:

buffer: 0.1M Hepes, 20 mM magnesium chloride, pH 6.8 substrate: 50 mM p-aminophenyl-p-galactoside (prepared from p-nitrophenyl-o-D-galactoside by hydration with hydrogen on Pd-carbon according to "Organikum" VEB Deutscher Verlag der Wissenschaften, 15th edition, Berlin 1976) in water neutraliser: 1N sodium hydroxidesolution indicator: 100 mg/ml 18-molybdodiphosphoric acid and 50 mg/ml phenyl-trimethylammonium chloride in water enzyme: 180 U/ml in buffer (the enzyme activity stated relates to the use of o-nitrophenol galactoside as substrate)

The following are mixed in a reaction vessel for the test:

| | |
|---|---|
| buffer | 780 μl |
| indicator | 100 μl |
| neutraliser | 20 μl |
| substrate | 100 μl |
| enzyme | a) 0, b) 1 μl, c) 2 μl, d) 3 μl, e) 4 μl, f) 5 μl |

After 4½ minutes incubation, it is centrifuged for ½ minute, the supernatant is discarded, the sediment dissolved in 1 ml dimethylsulphoxide and the absorbance (A) is measured immediately. The results in Table 3 are obtained.

TABLE 3

| μl enzyme | U/ml enzyme | A (800 nm) |
|---|---|---|
| 0 | 0 | 0.065 |
| 1 | 0.18 | 0.571 |
| 2 | 0.36 | 1.245 |
| 3 | 0.54 | 1.697 |
| 4 | 0.72 | 2.350 |
| 5 | 0.90 | 2.907 |

EXAMPLE 7

Determination of alkaline phosphatase (EC 3.1.3.1)

If in the recipe of Example 6, 50 mM p-amino phenylphosphate (prepared according to L. H. De Riemer, C. F. Meares, Biochemistry 20, 1606 (1981)) is used as substrate and 1M diethanolamine, 1 mM magnesium chloride, 0.1 mM zinc chloride, pH 9.8 is used as buffer, then the enzyme alkaline phosphatase can be determined with this. Using known concentrations of enzyme, a linear relation between enzyme concentration and absorbance at 800 nm is found as in Example 6.

EXAMPLE 8

Test carrier for the detection of γ-glutamyltransferase (EC 2.3.2.2)

A test carrier is manufactured analogous to Example 1, which, however, has the following alterations:

In the second reagent layer the buffer (2% by weight Keltrol F in 0.2M citrate buffer, pH 6.0) is replaced by 2% by weight Keltrol F in water, N,N-bis-(2-hydroxyethyl)-p-nitrosoaniline×HCl and glucose oxidase is omitted. A paper impregnated with substrate which is produced as follows is inserted between the transfer adhesive (2) and the second reagent layer (3):

A tea-bag paper (12 g/m$^2$) is impregnated with a solution of 250 mM glycylglycine and 20 mM γ-L-glutamyl-3-carboxyl-1,4-phenylenediamine (prepared according to U.S. Pat. 4,603,107 in 250 mM Tris buffer, pH 7.6 and dried for 20 minutes at 50° C.

A dilution series of γ-glutamyl transferase is prepared in 0.1M Tris buffer containing 10 mg/ml bovine serum albumin, pH 7.5. 10 μl of this solution is applied to a test carrier manufactured as described above. After one minute the remission values in percent at 37° C. and 950 nm cited in Table 4 are measured.

| Enzyme concentration U/ml | Remission at 950 nm in % |
|---|---|
| 0 | 59.0 |
| 0.245 | 57.0 |
| 0.471 | 55.5 |
| 1.31 | 52.7 |
| 2.77 | 49.7 |
| 4.93 | 45.8 |
| 7.39 | 42.2 |
| 9.85 | 39.0 |

The curve obtained in this way can be used to determine the unknown γ-glutamyl-transferase content in liquids.

EXAMPLE 9

Test carrier for the detection of acid phosphatase (EC 3.1.3.2)

In analogy to Example 8 a test carrier for the detection of acid phosphatase is obtained when the tea-bag paper is impregnated with 10 mM p-amino-phenylphosphate (prepared according to L. H. De Riemer, C. F. Meares, Biochemistry 20, 1606 (1981) in 0.1M citrate buffer, pH 5.0.

What is claimed is:

1. A reagent for the determination of an analyte comprising:
   a substance or substances capable of reacting with the analyte to form an organic amine which is a stronger reducing agent than aniline, and
   a sparingly soluble salt of a heteropoly acid which forms heteropoly blue with the organic amines wherein the cation of the sparingly soluble salt of the heteropoly acid is larger than $NH_4+$.

2. A reagent according to claim 1, wherein the heteropoly acid is a heteropoly acid of molybdenum, molybdenum and tungsten, vanadium and molybdenum or vanadium, molybdenum and tungsten with phosphorus, arsenic, silicon or germanium as the heteroatoms.

3. A reagent according to claim 2, wherein the heteropoly acid of molybdenum is 18-molybdodiphosphoric acid.

4. A reagent according to claim 1, wherein the cation is the formula $R^1R^2R^3R^4X+$ in which $R^1$, $R^2$, $R^3$ and $R^4$ are the same or different and denote hydrogen, or an alkyl, aryl or aralkyl residue, with the proviso that all of $R^1$, $R^2$, $R^3$ and $R^4$ are not hydrogen, or two alkyl residues may be taken together to form an alkylene residue, and X represents a phosphorus or a nitrogen atom.

5. A reagent according to claim 4, wherein X is a nitrogen atom.

6. A reagent according to claim 1 wherein the amine has the formula II

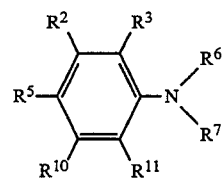

(II)

in which $R^5$ denotes hydroxy or amino, in which the amino group is optionally substituted once or twice by an alkyl residue, and the alkyl residue is itself optionally substituted by a hydroxy group, an amino group optionally substituted once or twice by alkyl, $PO_3H_2$, $SO_3H$ or $CO_2H$, and $R^6$ and $R^7$ which are both the same or different and represent hydrogen or alkyl, in which the alkyl residue is optionally substituted by a hydroxy group, an amino group optionally substituted once or twice by alkyl, $PO_3H_2$, $SO_3H$ or $CO_2H$, and $R^8$, $R^9$, $R^{10}$ and $R^{11}$ are the same or different and denote hydrogen, alkyl, alkoxy, alkylthio, aryloxy, arylthio, halogen, carboxy, carboxyalkyl or alkoxycarbonyl.

7. A reagent according to claim 1 which is in a solution.

8. A reagent according to claim 1 which is on a carrier.

* * * * *